United States Patent [19]

Ishimaru et al.

[11] 4,179,557

[45] Dec. 18, 1979

[54] ACYLATION OF 7-AMINOCEPHALOSPORANIC ACIDS

[75] Inventors: Toshiyasu Ishimaru, Suita; Yasutsugu Shimonishi, Nishinomiya; Hisayuki Sakurai, Osaka; Minoru Hatanaka, Takatsuki, all of Japan

[73] Assignee: President of Osaka University, Japan

[21] Appl. No.: 428,037

[22] Filed: Dec. 26, 1973

Related U.S. Application Data

[62] Division of Ser. No. 82,814, Oct. 21, 1970, abandoned.

[51] Int. Cl.$^2$ .................. C07D 501/04; C07D 501/06
[52] U.S. Cl. .................................. 544/28; 260/239.1; 544/29; 544/30
[58] Field of Search ............... 260/243 C; 544/28, 29, 544/30

[56] References Cited

U.S. PATENT DOCUMENTS 3,812,110   5/1974   Lee et al. .................. 260/243 C
3,842,072   10/1974   Heusler et al. ............ 260/243 C

*Primary Examiner*—Paul M. Coughlan, Jr.
*Attorney, Agent, or Firm*—Craig and Antonelli

[57] ABSTRACT

6-Aminoacylamidopenicillanic acid or 7-aminoacylamidocephalosporanic acids are produced in high yields by acylating 6-aminopenicillanic acid or 7-aminocephalosporanic acid with an amino acid, or a functional equivalent thereof, having its amino group protected with N,N-disubstituted β-keto acid amide, and then removing the protecting group from the resulting protected 6-aminoacylamidopenicillanic acid or protected 7-aminoacylamidocephalosporanic acid by hydrolysis.

24 Claims, No Drawings

ACYLATION OF 7-AMINOCEPHALOSPORANIC ACIDS

This is a division of application Ser. No. 82,814 filed Oct. 21, 1970, abandoned.

This invention relates to a process for producing penicillins, particularly 6-aminoacylamidopenicillanic acid, or cephalosporins, particularly 7-aminoacylamidocephalosporanic acids.

More particularly, this invention relates to a process for producing a 6-aminoacylamidopenicillanic acid represented by the formula (VI),

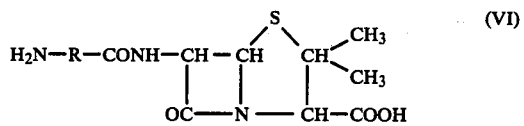

wherein $H_2N-R-CO-$ is an amino acid residue, [wherein R represents an alkylene group, or a residual group represented by the formula,

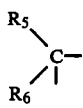

(wherein $R_5$ is a hydrogen atom or a methyl or methylthio group and $R_6$ is an alkyl, alkylthio, aryl, arylthio, arylalkyl, aryloxy or heterocyclic group, including the case where $R_5$ and $R_6$ jointly form a substituted- or unsubstituted-ring structure such as cycloalkyl or heterocyclic group)], or a nontoxic salt thereof, or a 7-aminoacylamidocephalosporanic acid represented by the formula (VII),

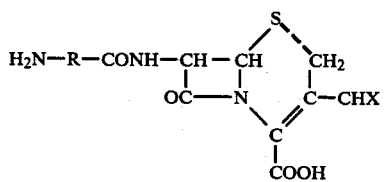

wherein R is the same as defined above and X is a hydrogen atom, an acetoxy group or a —S—Y group (wherein Y is an alkyl, alkenyl or a nucleophilic group), or a nontoxic salt thereof, which comprises acylating respectively 6-aminopenicillanic acid (hereinafter referred to as 6-APA) represented by the formula (I),

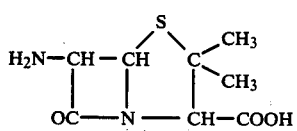

or a derivative thereof, or a 7-aminocephalosporanic acid (hereinafter referred to as 7-ACA) represented by the formula (II),

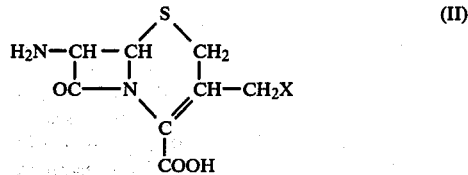

wherein X means the same as defined above, or a derivative thereof with an N-protected amino acid represented by the formula (III),

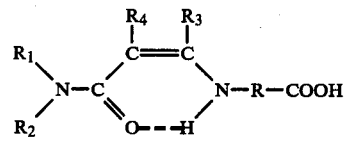

wherein $>N-R-COOH$ is an amino acid residue, (wherein R is the same as defined above), each of $R_1$ and $R_2$ is a lower alkyl group having 1 to 3 carbon atoms, including the case where $R_1$ and $R_2$ jointly form a piperidine ring or a morpholine ring and, $R_3$ is a lower alkyl group having 1 to 3 carbon atoms, $R_4$ is a hydrogen atom or a lower alkyl group having 1 to 3 carbon atoms, including the case where $R_3$ and $R_4$ jointly form a cyclopentenyl ring or a cyclohexenyl ring, or with a functional acid derivative of said protected amino acid to form correspondingly an N-protected 6-aminoacylamidopenicillanic acid represented by the formula (IV),

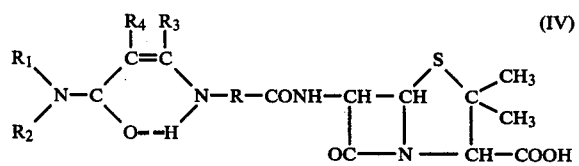

wherein $>N-R-CO-$ is an amino acid residue (wherein R is the same as defined above), and $R_1$, $R_2$, $R_3$ and $R_4$ are the same as defined above, or an N-protected 7-aminoacylamidocephalosporanic acid represented by the formula (V),

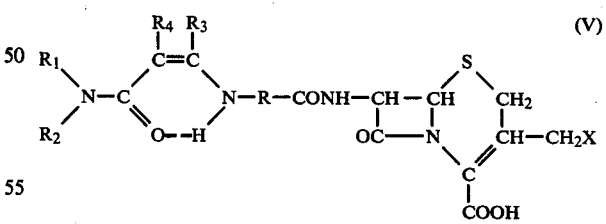

wherein R, $R_1$, $R_2$, $R_3$, $R_4$ and X are the same as defined above, and then hydrolyzing said N-protected 6-aminoacylamidopenicillanic acid or a salt thereof, or said N-protected 7-aminoacylamidocephalosporanic acid or a salt thereof.

The term "functional acid derivative" is used herein to include those derivatives in which a portion of the carboxyl group is replaced by other atoms or functional groups.

The salts, above referred to, include those with inorganic acids; with organic acids such as alkylsulfonic acids, benzenesulfonic acid, toluenesulfonic acid, or naphthylsulfonic acid; with metals such as sodium, potassium, calcium, magnesium, or aluminum; with ammonium and with substituted ammonium such as triethylamine, N,N-dimethylbenzylamine, N-alkylmorpholines, N-alkylpiperidines, procaine, or the like.

The aminopenicillins and cephalosporins produced according to the process of the present invention are important antibacterial substances as the therapeutic agents in men and animals in the treatment especially of infectious diseases caused by Gram-positive and Gram-negative bacteria.

For the preparation of 6-aminoacylamido-penicillanic acids (VI), there have been proposed a number of methods including those disclosed in Japanese Patent Publication Nos. 16,277/61, 4,064,65, 8,353/65, etc. However, none of these proposed methods can be said as having an industrial advantage because of low yield, complexity of the procedure, or low purity of the product. Among them, the methods that have been considered relatively advantageous are those disclosed in Japanese Patent Publication No. 15,947/67 and No. 20,315/67, which employ the functional acid derivative of an α-amino acid having its amino group protected by β-diketone or an ester of β-detoacid. Said methods, however, are not satisfactory from the industrial standpoint.

On the other hand, among various known methods for preparing 7-aminoacylamidocephalosporanic acids (VII), an industrially significant method is the one which utilizes a β-diketone or an ester of a β-diketoacid to protect the amino group in α-aminoacids. Such a method has already been reported in Journal of Medicinal Chemistry, Vol. 9, p. 746 (1966), Belgian Pat. No. 675,298, etc. As a result of the extensive investigation on more universal as well as more advantageous protecting groups, the present inventors have found quite unexpectedly that the intended product may be obtained in both the yield and purity far higher than those in conventional methods when the amino group of an amino acid is protected by an N,N-disubstituted β-ketoacid amide having the formula,

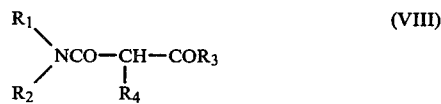

wherein $R_1$, $R_2$, $R_3$ and $R_4$ each means the same as mentioned before, said acid amide being an N,N-disubstituted acid amide which has the structure quite different from that of any known protecting agent mentioned above. Based on the finding, the present invention has been accomplished.

Moreover, while N-monoaryl-substituted acetoacetamide has been known to the art as a protecting agent, the specific N,N-disubstituted acid amide having the formula (VIII), in which $R_1$ and $R_2$ are selected as mentioned before, has the following advantages as a protecting agent over conventional ones: an alkali salt of the N-protected amino acid [formula (III)] can be produced in a high yield, and can be handled very conveniently owing to the lack of hygroscopicity and the ease of crystallization; and there are attained a higher yield of the condensation product [formula (IV) or formula (V)] of 6-APA or its salt or of 7-ACA or its salt with a functional acid derivative of said N-protected amino acid [formula (III)] and a higher yield of 6-aminoacylamidopenicillanic acid [formula (VI)] or of 7-aminoacylamidocephalosporanic acid [formula (VII)] after the hydrolysis of said condensation product, compared with those attained in known methods, the comparison being made on the basis of 6-APA or 7-ACA and under the same reaction conditions.

The N-protected amino acid (III) used in the present invention may be prepared by the condensation of an amino acid having the formula (IX) or its salt with an N,N-disubstituted β-ketoacid amide [formula (VIII)]. Said amino acid (IC) may be in optically active forms or in a racemic form.

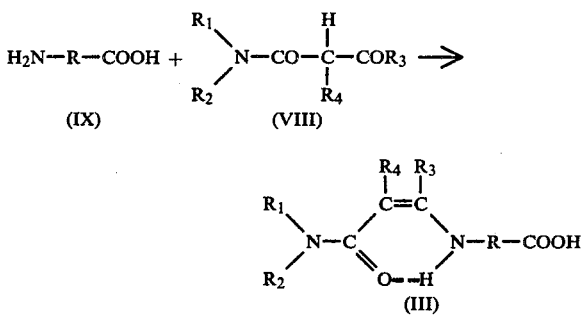

Since the N-protected amino acid (III) is supposed to exist in tautomeric forms, (IIIa) and (IIIb)

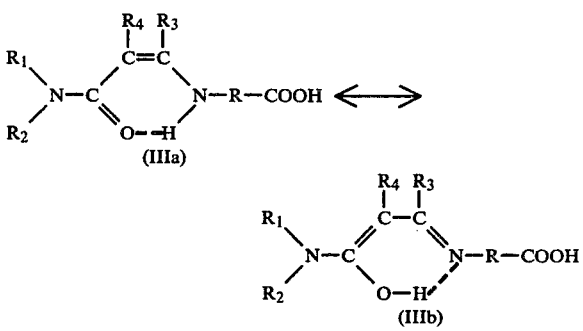

the N-protected 6-aminoacylamidopenicillanic acid (IV) or the N-protected 7-aminoacylamidocephalosporanic acid (V) derived therefrom is also supposed to exist in the similar tautomeric forms. However, for the sake of brevity, the structural formulas of (III), (IV) and (V) shall be assigned herein to tautomers of the amino acid, 6-aminoacylamidopenicillanic acid and 7-aminoacylamidocephalosporanic acid respectively, and their nomenclatures shall accord to said structural formulas. The dotted line in the formulas (III), (IIIa), (IIIb), (IV) and (V) represents a hydrogen bonding.

In the formula (IX) of an amino acid the grouping >N—R—COOH represents an amino acid residue having one or more amino groups at any position, and all of the amino groups shall be protected in the process of the present invention.

As the amino acid having the formula (IX), there may suitably be used a variety of those derived from aliphatic, arylaliphatic, aromatic, cycloaliphatic, or heterocyclic compounds. The most preferable amino acid is the one having an amino group at the α-position to the carboxyl group, which is represented by the formula,

wherein $R_5$ is a hydrogen atom, methyl group, methylthiomethyl group, etc.; $R_6$ is methylthioethyl, phenyl, nitrophenyl, aminophenyl, alkoxyphenyl, alkylphenyl, halogenophenyl, thienyl, methylthienyl, pyridyl, imidazole, thiazole, pyrazole, pyrazolone, isooxazole, isothiazole, pyrrole, furan, tetrahydropyrrole, tetrahydrothienyl, sydnone, cyclopentyl, or cyclohexyl radical; including the case where $R_5$ and $R_6$ jointly form a ring structure such as tetrahydrothienyl, cyclopentyl, cyclohexyl, or the like.

Typical examples of the N,N-disubstituted β-ketoacid amide having the formula (VIII), which is a protecting agent for the amino group in this invention, include N,N-dimethylacetoacetamide, N,N-diethylacetoacetamide, N-morpholinoacetoacetamide, 2-N,N-dimethylcarbamoylcyclopentanone, 2-N-morpholinocarbonylcyclopentanone, 2-N,N-dimethylcarbamoylcyclohexanone, etc. The most preferable protecting agents are N,N-dimethylacetoacetamide, N,N-diethylacetoacetamide, and N-morpholinoacetoacetamide.

According to the invention, 6-APA or its derivative, or 7-ACA or its derivative is acylated with a protected amino acid having the formula (III) or a functional acid derivative thereof. As the derivatives of 6-APA or 7-ACA there are used salts with alkali, alkaline earth and other metals, substituted amines, or silyl derivatives. Typical examples of the functional acid derivative of the protected amino acid having the formula (III) include mixed acid anhydrides formed by reacting said protected amino acid with, for example, dimethylacetyl halides, trimethylacetyl halides (pivalyl halides), diphenylacetyl halides, diethylacetyl halides, ethyl chloroformate, isobutyl chloroformate, or isopropyl chloroformate; intermediates formed by reacting said N-protected amino acid with carbodiimides such as N,N'-dicyclohexyl carbodiimide, N,N'-carbonylditriazole, N,N'-carbodiimidazole; and reactive esters of said protected amino acid such as p-methoxyphenyl ester, p-nitrophenyl ester, propargyl ester, carboxymethyl thioester, N-hydroxysuccinimide ester, or cyanomethyl ester.

The mixed acid anhydrides mentioned above can be obtained by treating a salt of an N-protected acid with a substituted acetic acid halide or alkyl chloroformate in the presence of a small amount of catalyst. The catalyst may be a tertiary base represented by the formula

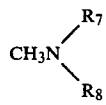

wherein each of $R_7$ and $R_8$ is a lower alkyl, a benzyl group or wherein $R_7$ and $R_8$ jointly form a morpholine or piperidine ring together with an oxygen or nitrogen atom.

The acylation of 6-APA or 7-ACA with such a functional acid derivative of the N-protected amino acid having the formula (III) is carried out preferably at a temperature below 0° C. in an aqueous solution containing an alkali metal salt of 6-APA or 7-ACA or a tertiary amine salt, such as triethylamine salt of 6-APA or 7-ACA, or in a mixed solvent containing water, or in an anhydrous solvent. As the organic solvent there may be used any inert solvent such as acetone, acetonitrile, isobutyl methyl ketone, methylene chloride, chloroform, ethylene dichloride, dimethylformamide, dioxane, tetrahydrofuran, ethylene glycol dimethyl ether, toluene, or dimethyl sulfoxide.

The N-protected 6-aminoacylamidopenicillanic acids (IV) or N-protected 7-aminoacylamidocephalosporanic acids (V) thus obtained are novel compounds. These compounds may be subjected to subsequent hydrolysis after being isolated or without being isolated. To obtain these compounds in a crystalline form, the above-mentioned reaction solution is filtered, the solvent is removed from the filtrate by distillation under reduced pressure, and to the residue is added ether, isopropyl ether, chloroform, etc., to obtain a salt of the N-protected compound of the formula (IV) or (V) in high yield.

The N-protected compounds of the formula (IV) or (V) are fairly soluble in common solvents, are relatively stable in nearly neutral solutions, and the infrared and ultraviolet absorption spectra thereof are quite different from those of the compounds of the formula (VI) or (VII), which are obtained on removing the protective group by hydrolysis.

In practicing the hydrolysis of the present process, the N-protected 6-aminoacylamidopenicillanic acid (IV) or a salt thereof or N-protected 7-aminocephalosporanic acid (V) or a salt thereof may be hydrolyzed either after being isolated or without being isolated. The hydrolysis is preferably effected in an aqueous solution or in a solvent containing water at a temperature below room temperature and at a pH of preferably lower than 5, brought about by the addition of a small amount of a diluted mineral acid of an aqueous solution of strong organic acid such as organic sulfonic acid, organophosphorus acid, formic acid, an aliphatic acid containing chlorine, or the like. After completion of hydrolysis, the resulting 6-aminoacylamidopenicillanic acid (VI) or salt thereof or 7-aminoacylamidocephalosporanic acid (VII) or salt thereof may be purified in a usual way by being extracted from the hydrolyzed mixture with a solvent such as, for example, isobutyl methyl ketone, acetic ester, chloroform, carbon tetrachloride, or methylene chloride, which will not dissolve the liberated protecting agent. Alternatively, it can be purified by crystallizing from the hydrolyzed mixture by adjusting the pH of the mixture.

The process of the present invention has proved particularly useful when applied to the production of aminobenzylpenicillin, 6-(1'-aminocyclohexylcarboamido)-penicillanic acid, 7-α-aminophenylacetamidocephalosporanic acid, 7-α-aminophenylacetamido-3-desacetoxycephalosporanic acid, or the like.

The 6-aminoacylamidopenicillanic acid and 7-aminoacylamidocephalosporanic acids produced according to the present process can exist in epimeric forms which are also included within the scope of the present invention.

According to the present process, the objective product can be obtained in high over-all yield for the reasons that (1) the N-protected amino acid of the formula (III) is stable and readily crystallizable and (2) after the N-acylation of 6-APA or 7-ACA, the protecting group at the N-position of 6-APA or 7-ACA can easily be removed under such a mild condition as the cleavage of the β-lactam ring of 6-APA or 7-ACA is not caused.

The following examples are given to illustrate the invention. However, the scope of the invention is not limited to the examples.

REFERENTIAL EXAMPLE 1

(a) Preparation of sodium salt of N-(1-N'-morpholinocarbonylpropen-2-yl)-α-aminophenylacetic acid.

5.0 Millimoles of D-phenylglycine was dissolved in an aqueous solution containing 5.0 millimoles of sodium hydroxide, and the solution was concentrated by evaporation under reduced pressure, and then brought to dryness. The dried product was dissolved in 50 ml of methanol or ethanol by warming. To the solution was added to 5.0 to 5.5 millimoles of N-morpholinoacetoacetamide, and the resulting mixture was heated on a water bath for 30 minutes. After cooling, the reaction mixture was filtered with suction, or the solution was evaporated to dryness under reduced pressure. The residue was dried overnight in vacuo over concentrated sulfuric acid or phosphorus pentoxide and then recrystallized from methanol or ethanol to give sodium salt of N-(1-N'-morpholinocarbonylpropen-2yl)-α-aminophenylacetic acid; melting point, 248° C. (decomp.); yield, 97%.

(b) The procedure in Referential Example 1(a) was repeated except that the N-morpholinoacetoacetamide was substituted by N,N-dimethylacetoacetamide, to obtain sodium salt of N-(1-N',N'-dimethylcarbamoylpropen-2-yl)-α-aminophenylacetic acid; melting point, 258° C. (decomp.); yield, 97%.

(c) In a similar way to that in Referential Example 1(a), following compounds were obtained using D-phenylglycine and potassium hydroxide in an equimolar proportion.

Potassium salt of N-(1-N'-morpholinocarbonylpropen-2-yl)-α-amino-2-phenylacetic acid; melting point, 214°–218° C. (decomp.); yield, 93%.

Potassium salt of N-(1-N',N'-diethylcarbamoylpropen- 2-yl)-α-amino-2-phenylacetic acid, melting point, 263°–264° C. (decomp.); yield, 87%.

Potassium salt of N-(1-N',N'-dimethylcarbamoylpropen-2-yl)-α-amino-2-phenylacetic acid; melting point, 212°–213° C. (decomp.); yield, 92%.

Potassium salt of N-(1-N'-piperidinocarbonylpropen-2-yl)-α-amino-2-phenylacetic acid; melting point, 216°–217° C. (decomp.); yield, 93%.

EXAMPLE 1

Preparation of D-α-aminobenzylpenicillin

5 Millimoles of pivalyl chloride was dissolved in 20 ml of dry acetone or dry tetrahydrofuran, and the solution was cooled to a temperature below −10° C. To the cooled solution was added a drop of N,N-dimethylbenzylamine or N-methylmorpholine with stirring. Then, to the stirred solution maintained at the same temperature was rapidly added 5 millimoles of a dry fine powder of sodium or potassium salt of N-(1-N'-morpholinocarbonylpropen-2-yl)-D-α-aminophenylacetic acid, and the solution was stirred for 30 minutes at the same temperature. On the other hand, 5 millimoles of 6-APA was dissolved in 15 ml of a 1:1 (by volume) mixture of acetone and water containing 5.5 to 6 millimoles of treithylamine, or in 15 ml of anhydrous methylene chloride containing 11 millimoles of treithylamine, and the solution was cooled to a temperature below −10° C. To the cooled solution was added the cooled solution of mixed acid anhydride prepared as mentioned above while being vigorously stirred and being maintained at a temperature below 0° C. After being stirred for about an hour at a temperature below 0° C., the mixture was further stirred at 2° C. to 5° C. for about 3 hours. The organic solvent was then removed by evaporation under reduced pressure. To the concentrated mixture was added about 10 ml of methyl isobutyl ketone or chloroform, and the mixture was stirred vigorously for additional 30 minutes while being added with 1 to 5N hydrochloric acid to maintain the pH at about 2. Then, the organic layer was removed and the aqueous layer was added with sodium hydrogencarbonate or triethylamine little by little to adjust the pH to 4.5 to 4.8, and was kept overnight at a temperature below 0° C. The precipitated crystals were isolated and purified in a usual way to obtain the intended product in a yield of 50 to 60%. Minimum inhibitory concentration of the product against *Escherichia coli* was found to be 6.3 γ/ml. Purity: 48% (by hydroxylamine method).

EXAMPLE 2

Preparation of D-α-aminobenzylpenicillin

5 Millimoles of a dry fine powder of potassium salt of N-(1N',N'-dimethylaminocarbonylpropen-2-yl)-D-α-aminophenylacetic acid was suspended in 15 ml of dry acetone, and the suspension was cooled to −45° C. To the cooled suspension were added 5 millimoles of ethyl chlorocarbonate and 2 drops of N-methylmorpholine, and the mixture was stirred for about one hour at the same temperature. Then 15 ml of methylene chloride containing 5 millimoles of triethylamine salt of 6-APA was added to said mixture at −45° C. with vigorous stirring. Reaction was allowed to proceed for one hour at said temperature. Then the temperature was gradually raised, and the reaction was allowed to continue for one hour at 0° C. and for additional 3 hours at 2° to 5° C. Then, most part of the organic solvent was removed under reduced pressure. The residue obtained was dissolved in 15 ml of chloroform, added with 10 ml of water, and the pH was adjusted to 1.5 by addition of 20%-hydrochloric acid while being cooled in ice and stirred vigorously. After being stirred for about 30 minutes, the organic layer was removed, and pH of the aqueous layer was adjusted to 5.0 by adding little by little triethylamine. The resulting solution was kept overnight in an ice cabinet, and the precipitated crystals were collected, washed with a small volume of cold 50%-methanol, then washed with ether, and dried. The yield was 82%, and the purity was 93%, as determined by biological assay and by chemical analysis using hydroxylamine.

EXAMPLE 3

Preparation of D-α-aminobenzylpenicillin

One gram of potassium salt of N-(1-N',N'-dimethylaminocarbonylpropen-2-yl)-D-α-aminophenylacetic acid was suspended in 15 ml of dry methylene chloride. A drop of N-methylmorpholine was added to the suspension at −10° C., and the suspension was cooled at −45° C. To the cooled suspension was added 3 ml of acetone containing 0.4 g of ethyl chlorocarbonate drop by drop over a period of 5 minutes. After the dropwise addition, reaction was allowed to proceed for 90 minutes at the same temperature. Then, to the reaction mixture was added at −45° C., 10 ml of methylene chloride containing 1.06 g of triethylamine salt of 6-aminopenicillanic acid dropwise over a period of 15 minutes. Reaction was allowed to proceed for one hour at −45° C. Then the temperature was gradually raised to 0° C., and the reaction solution was filtered to remove inorganic salts. The filtrate was concentrated to dryness under reduced pressure. Upon addition of dry ether the residue yielded 1.5 g (86.6%) of triethylamine salt of 6-[N-(1-N',N'-dimethylaminocarbonylpropen-2-yl)-D-α-aminophenylacetamido]penicillanic acid which was recrystallized from chloroform-ether to give white crystals melting at 191° C. (with foaming). IR (KBr), cm$^{-1}$: νC=O 1775, 1695, 1608. UV (CH$_2$Cl$_2$), λ$_{max}$, mμ: 230, 290.

In a manner similar to that mentioned above, the following compounds were obtained:

Triethylamine salt of 6-[N-(1-N',N'-diethylaminocarbonylpropen-2-yl)-D-α-aminophenylacetamido]penicillanic acid; white crystals; melting point, 193° C. (with foaming); yield, 79.6%.

Triethylamine salt of 6-[N-(1-morpholinocarbonylpropen-2-yl)-D-α-aminophenylacetamido]penicillanic acid; white crystals; decomposition point, 152° C.; yield, 89.8%.

Triethylamine salt of 6-[N-(1-piperidinocarbonylpropen-2-yl)-D-α-aminophenylacetamido]penicillanic acid; white crystals; melting point, 94° C. (with foaming); yield, 90.8%.

One gram of the above-obtained triethylamine salt of 6-[N-(-N,N-dimethylaminocarbonylpropen-2-yl)-D-α-aminophenylacetamido]penicillanic acid was dissolved in a mixture of 10 ml of methyl isobutyl ketone and 3 ml of water. While being cooled in ice and stirred, the pH of the solution was adjusted to 1.5 by addition of 20%-hydrochloric acid. After the solution was kept cooled and stirred for one hour, the insoluble matter was filtered off. The pH of the filtrate was adjusted to 5 to 5.5, and the filtrate was kept overnight in an ice cabinet. The precipitated crystals were collected by filtration, washed with 50%-acetone and then with acetone to give 0.51 g of white crystals melting at 192°-205° C. The purity was 91% as determined by biological assay.

EXAMPLE 4

Preparation of D-α-aminobenzylpenicillin

The procedure described in Example 2 was repeated using potassium salt of N-(1-N',N'-diethylaminocarbonylpropen-2-yl)-D-α-aminophenylacetic acid; yield, 78%; purity, 91%.

EXAMPLE 5

Preparation of D-α-aminobenzylpenicillin

The procedure described in Example 2 was repeated using potassium salt of N-(1-N'-morpholinocarbonylpropen-2-yl)-D-α-aminophenylacetic acid; yield, 75%; purity, 90%.

REFERENTIAL EXAMPLE 2

Preparation of sodium salt of N-(2-N'-morpholinocarbonylcyclopent-b 1-yl)-α-aminophenylacetic acid 2-Ethoxycarbonylcyclopentanone and morpholine were caused to react by heating in ethanol to yield 2-N-morpholinocarbonylcyclopentanone boiling at 190°-194° C. (4 mmHg), which was reacted with sodium salt of D-phenylglycine according to the procedure described in Referential Example 1(a) to obtain the captioned condensation product melting at 233°-236° C. (decomp.) in a yield of 83%.

EXAMPLE 6

Preparation of D-α-aminobenzylpenicillin.

The sodium salt of N-(2-N'-morpholinocarbonylcyclopent-1-yl)-α-aminophenylacetic acid obtained in Referential Example 2 was reacted with 6-APA according to the procedure described in Example 1, and then the reaction product was hydrolyzed; yield, 54%, purity, 67%.

REFERENTIAL EXAMPLE 3

Preparation of sodium salt of N-(1'-N'-morpholinocarbonylpropen-2'-yl)-α-amino-2-thienylacetic acid The sodium salt of DL-α-amino-2-thienylacetic acid [Chemical Abstracts, Vol. 51, p. 4944 (1957)] was reacted with morpholinoacetoacetamide according to the procedure described in Referential Example 1(a) to obtain the captioned compound melting at 154°-160° C. (decomp.) in a yield of 95%.

EXAMPLE 7

Preparation of DL-α-amino-2'-thienylmethylpenicillin

5 Millimoles of isobutyl chloroformate was dissolved in 15 ml of anhydrous acetonitrile containing a drop of N-methylmorpholine, and the solution was cooled to a temperature below −10° C. To the cooled solution was added 5 millimoles of sodium salt of N-(1-N'-morpholinocarbonylpropen-2-yl)-α-amino-2'-thienylacetic acid, and stirred for 20 minutes at the same temperature. On the other hand, 5 millimoles of 6-APA was dissolved in 15 ml of water containing 5.5 ml of triethylamine, then diluted with 15 ml of acetone, and cooled to −8° C. To the cooled solution was added rapidly with vigorous stirring the above-obtained solution of mixed acid anhydride while maintaining the reaction temperature below 0° C. After about one hour of stirring, the mixture was further stirred at 2° to 5° C. for additional 3 hours, after which the organic solvent was removed under reduced pressure. To the resulting concentrated aqueous solution was added 20 ml of isobutyl methyl ketone, and the solution was vigorously stirred at 10° to 15° C. while maintaining the pH at about 2.5 by addition of 30%-nitric acid. Then, the organic layer was removed and the aqueous layer, the pH of which was adjusted to 5 by addition of triethylamine, was freeze-dried to obtain crude α-amino-2'-thienylmethylpenicillin which showed a minimum inhibitory concentration of 25 γ/ml against *Escherichia coli*.

REFERENTIAL EXAMPLE 4

Preparation of sodium salt of N-(1-N'-morpholinocarbonylpropen-2-yl)-α-amino-γ-methylthiobutyric acid DL-Methionine sodium salt was reacted with N-morpholinoacetoacetamide according to the procedure described in Referential Example 1(a); melting point, 98°-102° C.; yield, 76%.

REFERENTIAL EXAMPLE 5

Preparation of sodium salt of N-(1-N',N'-dimethylcarbamoylpropen-2-yl)-1-aminocyclohexylcarboxylic acid The sodium salt of 1-aminocyclohexylcarboxylic acid [Chemische Berichte, Vol. 19, p. 1722 (1906)] was reacted with N,N-dimethylacetoacetamide; melting point, 242°–245° C. (decomp.); yield, 94%.

EXAMPLE 8

Preparation of 6-(α-amino-γ-methylthiobutyrylamido)penicillanic acid

The sodium salt of N-(1-N'-morpholinocarbonylpropen-2-yl)-α-amino-γ-methylthiobutyric acid obtained in Referential Example 4 was reacted with 6-APA according to the procedure described in Example 1, and then the reaction product was hydrolyzed; yield, 50%; minimum inhibitory concentration against *Escherichia coli*, 25 γ/ml.

EXAMPLE 9

Preparation of 6-(1-aminocyclohexylcarboxamido)penicillanic acid

The sodium salt of N-(1-N',N'-dimethylcarbamoylpropen-2-yl)-1-aminocyclohexylcarboxylic acid obtained in Referential Example 5 was reacted with 6-APA according to the procedure described in Example 1, and then the reaction product was hydrolyzed; yield, 43%, minimum inhibitory concentration against *Escherichia coli*, 50 γ/ml.

EXAMPLE 10

Preparation of 7-(1'-N',N'-dimethylcarbamoylpropen-2'-yl)-α-aminophenylacetamidocephalosporanic acid (X=OCOCH₃) and hydrolysis thereof to prepare 7-α-aminophenylacetamidocephalosporanic acid (X=OCOCH₃)

5 Millimoles of isobutyl chloroformate was dissolved in 20 ml of dry acetone or acetonitrile, and the solution was cooled to a temperature below −10° C. To the cooled solution was added a drop of N,N-dimethylbenzylamine or N-methylmorpholine. Then, to the solution maintained at the same temperature was added 5 millimoles of the aforementioned sodium salt of N-(1-N',N'-dimethylcarbamoylpropen-2-yl)-α-aminophenylacetic acid, and the solution was stirred for 30 minutes.

On the other hand, 5 millimoles of 7-ACA was dissolved in 15 ml of acetonitrile-water (1:1 by volume) containing 5.5 millimoles of triethylamine or sodium hydrogencarbonate, and the solution was cooled to a temperature below −8° C. To the cooled solution was rapidly added with vigorous stirring the cooled solution of mixed acid anhydride prepared as mentioned above while being maintained at a temperature below 0° C. After stirring for 30 minutes, 4 g of sodium chloride was added to the reaction mixture, and further stirred for 30 minutes at 0° C. Then, the organic layer was separated and evaporated to dryness under reduced pressure. The resulting sirup was admixed with 30 ml of isobutyl methyl ketone-water (10:3 by volume) containing 1.8 ml of 80%-formic acid, stirred for 30 minutes, and thereafter kept at a temperature below 0° C. for 20 hours. The crystals were collected by centrifugal precipitation, then suspended in 10 ml of acetonitrile, again subjected to centrifugal precipitation, and finally dried in vacuo.

The yield of the crystals was 60%, and the crystals showed a single spot on the paper chromatogram (butanol:acetic acid:water=3:1:1 by volume). Minimum inhibitory concentration against *Escherichia coli* was 10 γ/ml.

EXAMPLE 11

Preparation of 7-(α-amino-2'-thienylacetamido)cephalosporanic acid (X=OCOCH₃)

5 Millimoles of pivalyl chloride was dissolved in 20 ml of dry tetrahydrofuran, and the solution was cooled to a temperature below −10° C. To the cooled solution was added a drop of N-methylmorpholine. Then, to the solution maintained at the same temperature was added 5 millimoles of the sodium salt of N-(1'-N'-morpholinocarbonylpropen-2'-yl)-α-amino-2-thienylacetic acid obtained in Referential Example 3, and the mixture was stirred for 30 minutes. On the other hand, 5 millimoles of 7-ACA was dissolved in 15 ml of acetone-water (1:1 by volume) containing 5.5 millimoles of sodium hydrogencarbonate or triethylamine and the solution was cooled to a temperature below −8° C. To the cooled solution was rapidly added with vigorous stirring the cooled solution of mixed acid anhydride prepared as mentioned above while maintaining the reaction temperature below 0° C. After being stirred for 30 minutes at the same temperature, the mixture was further stirred at 0° C. for additional one and a half hours, and then the organic solvent was removed by distillation at a low temperature. To the concentrated aqueous solution, after being cooled, was added 30 ml of isobutyl methyl ketone, and then was added thereto with vigorous stirring at 0° C. 4 ml of cold water containing 1.8 ml of 80%-formic acid in small portions. The mixture was stirred for 30 minutes, and thereafter kept at a temperature below 0° C. for 20 hours to precipitate crystals. The crystals were collected by centrifugal precipitation, and purified according to the common procedure to obtain the captioned product in a yield of 65%, which showed a single spot on the paper chromatogram. Minimum inhibitory concentration against *Escherichia coli* was 20 γ/ml.

EXAMPLE 12

Preparation of 7-(α-amino-2'-thienylacetamido)-desacetoxycephalosporanic acid (X=H)

The sodium salt of N-(1'-N'-morpholinocarbonylpropen-2'-yl)-α-amino-2-thienylacetic acid obtained in Referential Example 3 was reacted with 7-amino-3-desacetoxycephalosporanic acid (X=H) [Journal of Medicinal Chemistry, Vol. 7, p. 118 (1964)] according to the procedure described in Example 10, and then the reaction product was hydrolyzed; yield, 70%; minimum inhibitory concentration against *Escherichia coli*, 40 γ/ml.

EXAMPLE 13

7-N-(α-Aminophenylacetamido)cephalosporanic acid

5 Millimoles of a dry fine powder of potassium salt of N-(1-N',N'-dimethylcarbamoylpropen-2-yl)-D-α-aminophenylacetic acid obtained in Referential Example 1(c) was suspended in 15 ml of dry acetone, and the suspension was cooled to −45° C. To the cooled suspension were added 5 millimoles of ethyl chlorocarbonate and 2 drops of N-methylmorpholine, and the mixture was stirred for about one hour at the same temperature. Then 15 ml of methylene chloride containing 5 millimoles of triethylamine salt of 7-ACA was added to said mixture at −45° C. with vigorous stirring. Reaction was allowed to proceed for one hour at said temperature. Then the temperature was gradually raised, and the reaction was allowed to continue for one hour at 0° C. and for additional 3 hours at 2° to 5° C. Then, most part of the organic acid was removed by distillation under reduced pressure. The residue obtained was dissolved in 15 ml of chloroform, added with 10 ml of water, and the pH was adjusted to 2.0 by addition of 50%-formic acid while being cooled in ice and stirred. After being stirred for about 30 minutes, the organic layer was removed, and pH of the aqueous layer was adjusted to 4.5 by adding triethylamine in small portions. The resulting solution was kept overnight in an ice cabinet, and the precipitated crystals were collected, washed with a small volume of cold 50%-methanol, then washed with ether, and dried. The yield was 82%, and the purity was 92%, as determined by biological assay and by chemical analysis using hyrodxylamine.

The above-said procedure was repeated under the same conditions of reaction and subsequent treatment except that 30 ml of 50%-acetone was used in place of the methylene chloride; yield, 83%, purity 92%.

EXAMPLE 14

7-N-(α-aminophenylacetamido)-3-desacetoxycephalosporanic acid

5 Millimoles of the potassium salt of N-(1-N',N'-dimethylcarbamoylpropen-2-yl)-D-α-aminophenylacetic acid obtained in Referential Example 1(c) was reacted with 5 millimoles of triethylamine salt of 7-amino-3-desacetoxycephalosporanic acid and subsequently treated according to the procedure described in Example 13; yield, 82%; purity, 92% as determined by biological assay and by chemical analysis using hydroxylaine.

What is claimed is:

1. In a process for producing a member selected from the group consisting of
   (a) a 7-aminoacylamidocephalosporanic acid represented by the formula:

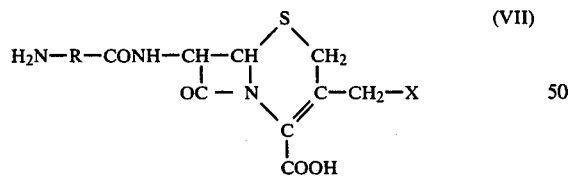

and
   (b) a non-toxic salt of said 7-aminoacylamidocephalosporanic acid, wherein R is an alkylene group or

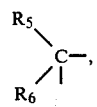

wherein $R_5$ is selected from the group consisting of a hydrogen atom, a methyl group and a methylthio group and $R_6$ is selected from the group consisting of an alkyl, alkylthio, aryl, arylthio, arylalkyl, aryloxy and hetercyclic groups, $R_5$ and $R_6$ together representing a substituted or unsubstituted cycloalkyl or heterocyclic group, X is selectd from the group consisting of hydrogen atom, acetoxy group, and S—Y wherein Y is an alkyl, alkenyl, or nucleophilic group, wherein a 7-aminocephalosporanic acid or derivatives thereof are acylated with an N-protected amino acid and the resulting product is hydrolyzed followed by separation and recovery of said group member, the improvement which comprises:

(A) acylating the 7-aminocephalosporanic acid represented by the formula

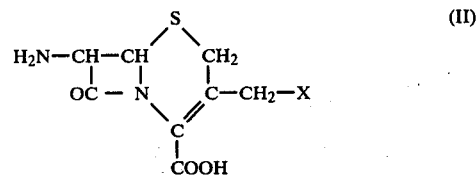

where X is defined as above, or derivatives thereof with a N-protected amino acid represented by the formula,

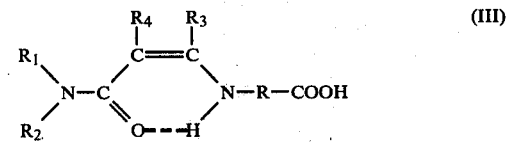

or functional acid derivative thereof, wherein R is the same as defined above, $R_1$ and $R_2$ each is a lower alkyl group having 1 to 3 nitrogen atom, $R_1$ and $R_2$ when taken together jointly form with the carbon atoms attached thereto a piperidine ring or a morpholine ring, $R_3$ is a lower alkyl group having 1 to 3 carbon atoms, $R_4$ is a hydrogen atom or a lower alkyl group having 1 to 3 carbon atoms, $R_3$ and $R_4$ when taken together jointly form with the carbon atoms attached thereto a cyclopentenyl ring or a cyclohexenyl ring to form the corresponding N-protected 7-aminoacylamidocephalosporanic acid represented by the formula:

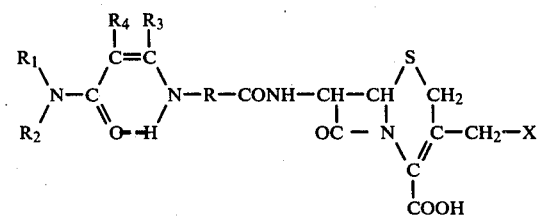

2. The process according to claim 1, wherein $R_1$, $R_2$ and $R_3$ are all lower alkyl groups having 1 to 3 carbon atoms, $R_4$ is a lower alkyl group having 1 to 3 carbon atoms or a hydrogen atom, $R_1$ and $R_2$ taken together represent a piperidine or morpholine ring, $R_3$ and $R_4$ taken together represent a cyclopentenyl ring and R is selected from the group consisting of a lower alkylene group and a group represented by the formula

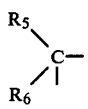

wherein R₅ is selected from the group consisting of a hydrogen atom, a methyl group, and a methylthio group, and R₆ is a radical selected from the group consisting of methylthioethyl, phenyl, nitrophenyl, aminophenyl, alkoxyphenyl, alkylphenyl, halogenophenyl, thienyl, methylthienyl, pyridyl, imidazole, pyrrol, furan, tetrahydropyrrole, tetrahydrothienyl, sydnone, cyclopentyl and cyclohexyl or wherein R₅ and R₆ jointly form tetrahydrothienyl, cyclopentyl or cyclohexyl.

3. The process according to claim 1, wherein said functional acid derivative is mixed acid anhydride.

4. The process according to claim 3, wherein said mixed acid anhydride is formed by reacting said protected amino acid with a member selected from the group consisting of dimethylacetyl halides, trimethylacetyl halides, diphenylacetyl halides, diethylacetyl halides, ethyl chloroformate, isobutyl chloroformate and isopropyl chloroformate.

5. The process according to claim 1, wherein said X is selected from the group consisting of hydrogen atom and acetoxy group.

6. The process according to claim 1, wherein said 7-aminocephalosporanic acid or salts thereof are acylated with said functional acid derivative of said N-protected amino acid in an anhydrous solvent.

7. The process according to claim 1, wherein said 7-aminocephalosporanic acid or salts thereof are acylated with said functional acid derivative of said N-protected amino acid in a water-containing solvent.

8. The process according to claim 1, wherein said N-protected amino acid or salt thereof is hydrolyzed with a member selected from the group consisting of a dilute mineral acid and a strong organic acid.

9. The process according to claim 1, wherein said N-protected amino acid or salt thereof formed is simultaneously hydrolyzed.

10. The process according to claim 1, wherein said functional acid derivative is an intermediate formed by reacting said N-protected amino acid with a carbodiimide selected from the group consisting of N,N'-dicyclohexyl carbodiimide and N,N'-carbonylditriazole.

11. The process according to claim 1, wherein said functional derivative is an activated ester selected from the group consisting of p-methoxyphenyl ester, p-nitrophenyl ester, propargyl ester, carboxymethylthio ester, N-hydroxysuccinimide ester, and cyanomethyl ester.

12. The process according to claim 1, wherein said acylation is carried out at a temperature below 0° C. in an aqueous solution comprising an alkali metal salt of said 7-aminocephalosporanic acid, or a tertiary amine salt of said 7-aminocephalosporanic acid.

13. The process according to claim 12, wherein said aqueous solution contains an organic solvent.

14. The process according to claim 13, wherein said organic solvent is selected from the group consisting of acetone, acetonitrile, isobutyl methyl ketone, methylene chloride, chloroform, ethylene dichloride, dimethylformamide, dioxane, tetrahydrofuran, ethylene glycol dimethyl ether, toluene and dimethyl sulfoxide.

15. The process according to claim 6, wherein said solvent is selected from the group consisting of acetone, acetonitrile, isobutyl methyl ketone, methylene chloride, chloroform, ethylene dichloride, dimethylformamide, dioxane, tetrahydrofuran, ethylene glycol dimethyl ether, toluene and dimethyl sulfoxide.

16. The process according to claim 15, wherein said functional acid derivative is a mixed acid anhydride.

17. The process according to claim 1, wherein said 7-aminocephalosporanic acid or salts thereof are acylated with said functional acid derivative of said N-protected amino acid in an anhydrous solvent.

18. The process according to claim 17, wherein said solvent is selected from the group consisting of acetone, acetonitrile, isobutyl methyl ketone, methylene chloride, chloroform, ethylene dichloride, dimethylformamide, dioxane, tetrahydrofuran, ethylene glycol dimethyl ether, toluene and dimethyl sulfoxide.

19. The process according to claim 18, wherein said functional acid derivative is a mixed acid anhydride.

20. The process according to claim 2, wherein said 7-aminocephalosporanic acid or salts thereof are acylated with said functional acid derivative of said N-protected amino acid in an anhydrous solvent.

21. The process according to claim 20, wherein said solvent is selected from the group consisting of acetone, acetonitrile, isobutyl methyl ketone, methylene chloride, chloroform, ethylene dichloride, dimethylformamide, dioxane, tetrahydrofuran, ethylene glycol dimethyl ether, toluene and dimethyl sulfoxide.

22. The process according to claim 21, wherein said functional acid derivative is a mixed acid anhydride.

23. A process for producing 7-aminoacrylamidocephalosporanic acid represented by the formula:

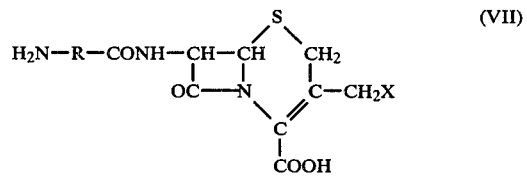

wherein R is a group

wherein R₅ is a hydrogen atom, R₆ is a phenyl group and X is selected from the group consisting of hydrogen atom and acetoxy group, which comprises:

(A) acylating the 7-aminocephalosporanic acid represented by the formula:

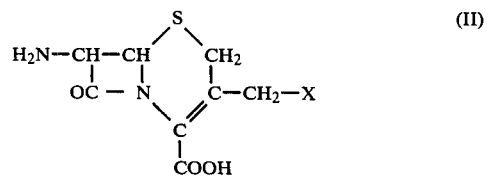

wherein X is the same as defined above, with an N-protected amino acid represented by the formula:

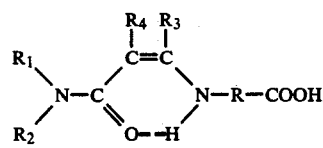 (II)

wherein R is the same as defined above, $R_1$ and $R_2$ each is a lower alkyl group having 1 to 3 carbon atoms, when taken together $R_1$ and $R_2$ jointly formed with the nitrogen atom attached thereto a piperidine ring or a morpholine ring, $R_3$ is a lower alkyl group having 1 to 3 carbon atoms, $R_4$ is a hydrogen atom or a lower alkyl group having 1 to 3 carbon atoms, $R_3$ and $R_4$ when taken together jointly form with the carbon atoms attached thereto a cyclopentenyl ring, to form the corresponding N-protected 7-aminoacylamidocephalosporanic acid represented by the formula,

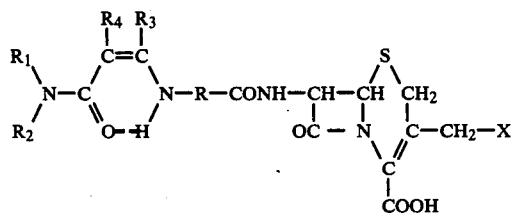 (V)

wherein R, $R_1$, $R_2$, $R_3$ and $R_4$ and X are the same as defined above, (B) hydrolyzing said N-protected 7-aminoacylamidocephalosporanic acid; and (C) separating and recovering said 7-aminoacylamidocephalosporanic acid.

24. A compound selected from the group consisting of a cephalosporin of the formula:

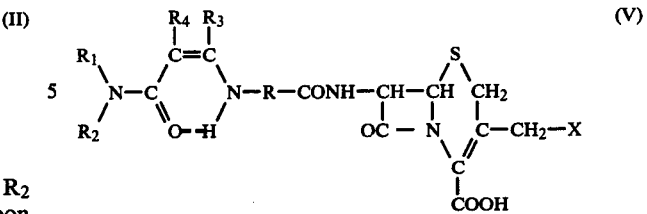 (V)

and a non-toxic salt thereof, wherein R is selected from the group consisting of

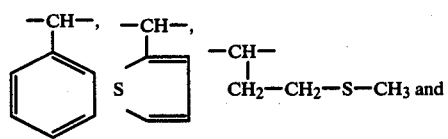

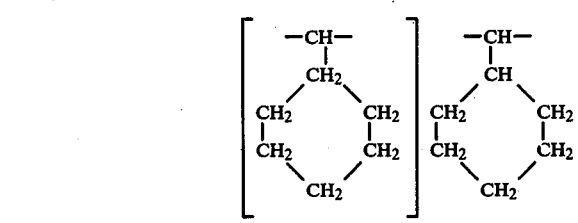

X is selected from the group consisting of hydrogen atom and acetoxy group, $R_1$ and $R_2$ each is methyl or ethyl or jointly form together with the nitrogen atom attached thereto a piperidine ring or a morpholine ring, $R_3$ is a lower alkyl group having 1 to 3 carbon atoms, $R_4$ is a hydrogen atom or a lower alkyl group having 1 to 3 carbon atoms, $R_3$ and $R_4$ when taken together jointly form with the carbon atoms attached thereto a cyclopentenyl ring.

* * * * *